(12) United States Patent
Krull et al.

(10) Patent No.: US 8,899,049 B2
(45) Date of Patent: Dec. 2, 2014

(54) SYSTEM AND METHOD FOR CONTROLLING COMBUSTOR OPERATING CONDITIONS BASED ON FLAME DETECTION

(75) Inventors: Anthony Wayne Krull, Anderson, SC (US); Nan Zong, Simpsonville, SC (US); Danielle Marie Kalitan, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 1001 days.

(21) Appl. No.: 12/986,227

(22) Filed: Jan. 7, 2011

(65) Prior Publication Data
US 2012/0174590 A1    Jul. 12, 2012

(51) Int. Cl.
*F23R 3/28*    (2006.01)
*F23N 5/08*    (2006.01)
*G01J 5/06*    (2006.01)
*G01J 5/08*    (2006.01)
*G01J 5/00*    (2006.01)
*G01N 21/72*   (2006.01)

(52) U.S. Cl.
CPC ............ *F23R 3/286* (2013.01); *F23N 5/082* (2013.01); *G01J 5/0018* (2013.01); *G01J 5/0088* (2013.01); *G01J 5/061* (2013.01); *G01J 5/0806* (2013.01); *G01J 5/0821* (2013.01); *F23N 2900/05005* (2013.01); *G01N 21/72* (2013.01)
USPC ................................ 60/742; 60/740; 356/432

(58) Field of Classification Search
CPC ............ F23R 3/60; F23R 3/286; F23N 5/082; F23N 2900/05005; G01J 5/008; G01J 5/061; G01J 5/0806; G01J 5/0821; G01J 5/0088; G01J 5/0018; G01N 21/72
USPC ............. 60/740, 742, 737, 746, 747; 356/432
See application file for complete search history.

(56) References Cited

U.S. PATENT DOCUMENTS

| | | | |
|---|---|---|---|
| 3,689,773 A * | 9/1972 | Wheeler ....................... 250/554 |
| 4,709,155 A * | 11/1987 | Yamaguchi et al. .......... 250/554 |
| 4,983,853 A * | 1/1991 | Davall et al. ................. 250/554 |
| 5,071,105 A * | 12/1991 | Donze et al. .................... 266/51 |
| 5,180,227 A | 1/1993 | John et al. |
| 5,845,480 A | 12/1998 | DeFreitas et al. |
| 5,857,320 A * | 1/1999 | Amos et al. ..................... 60/776 |
| 5,978,525 A | 11/1999 | Shu et al. |
| 6,141,098 A | 10/2000 | Sawatari et al. |
| 6,278,374 B1 | 8/2001 | Ganeshan |
| 6,599,028 B1 | 7/2003 | Shu et al. |
| 6,978,074 B2 | 12/2005 | Shu et al. |
| 7,320,213 B2 | 1/2008 | Shah et al. |
| 7,334,413 B2 | 2/2008 | Myhre |
| 7,336,882 B1 | 2/2008 | Ptasinski et al. |
| 7,461,509 B2 | 12/2008 | Mick et al. |
| 7,484,369 B2 * | 2/2009 | Myhre ............................ 60/803 |
| 7,489,835 B1 | 2/2009 | Xia et al. |

(Continued)

*Primary Examiner* — William H Rodriguez
*Assistant Examiner* — Carlos A Rivera
(74) *Attorney, Agent, or Firm* — Dority & Manning, PA

(57) ABSTRACT

A system is disclosed that includes a combustor having an end cover and at least one fuel nozzle assembly extending from an inner face of the end cover. A cartridge may extend through the end cover and into the fuel nozzle assembly. The cartridge may define an opening for receiving light emitted from within the combustor. Additionally, a fiber optic cable may be disposed within the cartridge and may be configured to capture at least a portion of the light received through the opening.

20 Claims, 5 Drawing Sheets

(56) References Cited

U.S. PATENT DOCUMENTS

| | | |
|---|---|---|
| 7,492,980 B2 | 2/2009 | McCarthy et al. |
| 7,628,137 B1 * | 12/2009 | McAlister .................... 123/297 |
| 2005/0278108 A1 | 12/2005 | Norman et al. |
| 2010/0140373 A1 | 6/2010 | Myhre et al. |
| 2010/0183993 A1 * | 7/2010 | McAlister .................... 431/254 |
| 2010/0220182 A1 | 9/2010 | Krull et al. |
| 2011/0048371 A1 * | 3/2011 | McAlister .................... 123/297 |
| 2011/0048381 A1 * | 3/2011 | McAlister .................... 123/472 |
| 2011/0056458 A1 * | 3/2011 | McAlister .................... 123/297 |
| 2011/0057058 A1 * | 3/2011 | McAlister .................. 239/533.3 |
| 2011/0132319 A1 * | 6/2011 | McAlister .................... 123/297 |
| 2011/0146619 A1 * | 6/2011 | McAlister .................... 123/297 |
| 2011/0233308 A1 * | 9/2011 | McAlister .................. 239/533.2 |

\* cited by examiner

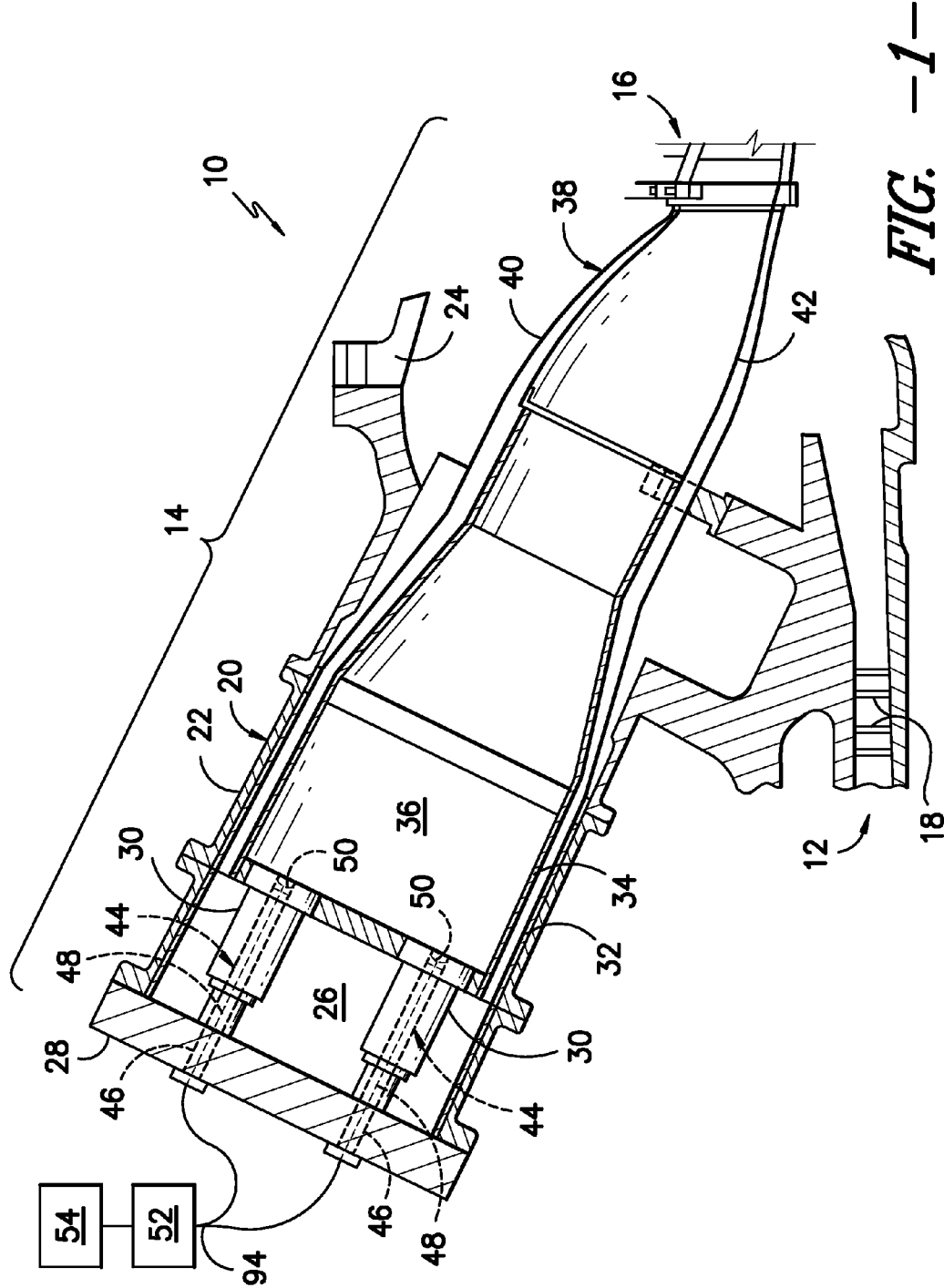

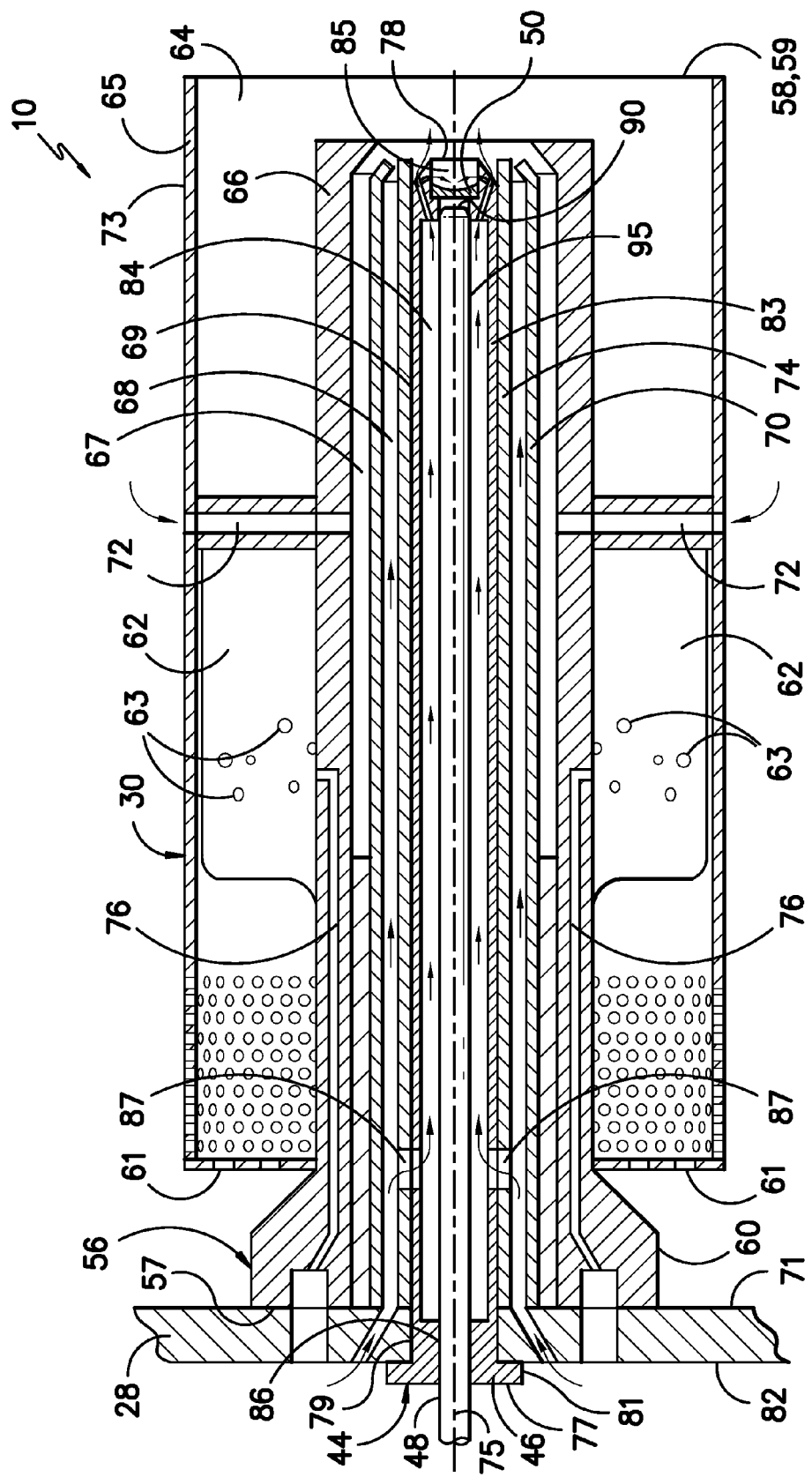
FIG. -2-

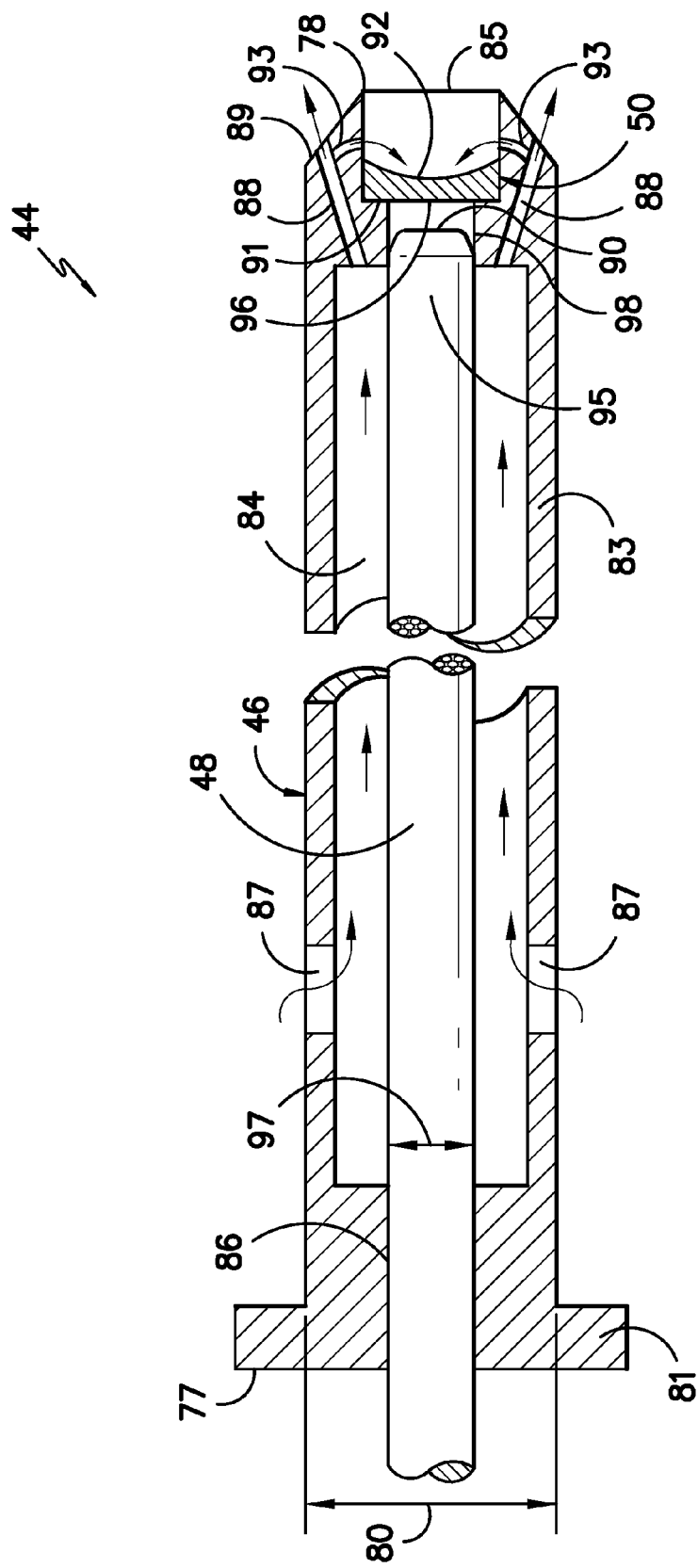
FIG. -3-

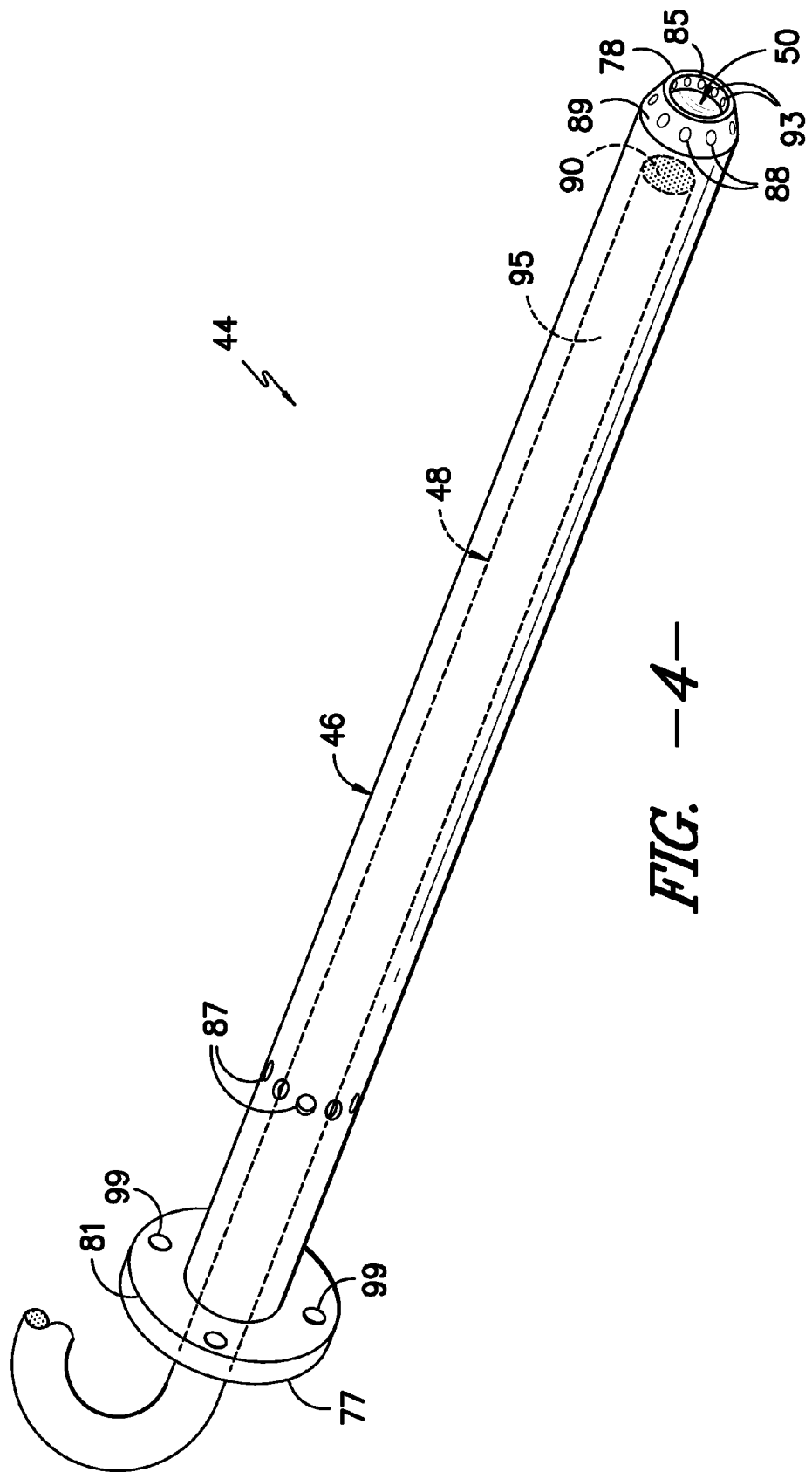
FIG. -4-

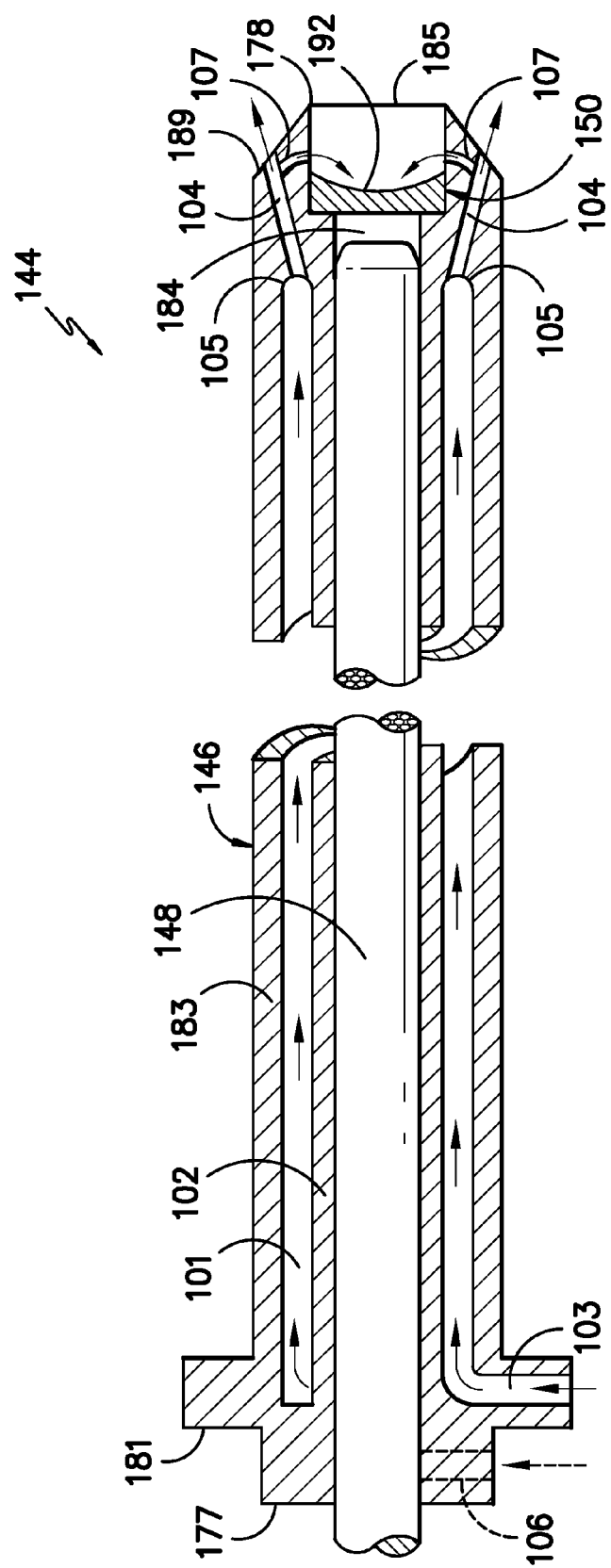
FIG. -5-

SYSTEM AND METHOD FOR CONTROLLING COMBUSTOR OPERATING CONDITIONS BASED ON FLAME DETECTION

FIELD OF THE INVENTION

The present subject matter relates generally to gas turbines and, more particularly, to a system and method for controlling operating conditions of a gas turbine combustor based on the detection of light from the combustor's flames.

BACKGROUND OF THE INVENTION

Gas turbines typically include a compressor section, a combustion section, and a turbine section. The compressor section pressurizes air flowing into the gas turbine. The pressurized air discharged from the compressor section flows into the combustion section, which is generally characterized by a plurality of combustors disposed around an annular array about the axis of the engine. Air entering each combustor is mixed with fuel and combusted. Hot gases of combustion flow from each combustor to the turbine section of the gas turbine to drive the turbine and generate power.

During the operation of a gas turbine, anomalies may occur within the turbine's combustors that increase emissions of regulated combustion products, reduce combustor efficiency and/or reduce the part life of components within the combustor. For example, excessive flame temperatures within the combustor may cause over-firing conditions, thereby resulting in damage to the turbine's components. Additionally, excessive flame temperatures can lead to increased emissions and may necessitate increased cooling flow to the combustor, thereby reducing combustor efficiency. Similarly, lean blowout (LBO) events, characterized by extinguished flames due to an air/fuel mixture that is too lean, increase emissions and also reduce combustor efficiency. Thus, without proper detection and mitigation of such undesirable operating conditions, a gas turbine may be not meet emissions standards, may suffer reduced longevity and/or may operate at reduced efficiencies.

Systems are known that provide for the detection of combustor operating conditions through visualization of a combustor's flame. However, such systems are typically very difficult to install within and/or remove from the combustor. As such, when a component of the system is damaged or must otherwise be replaced, a significant amount of time and money must be spent to remove and re-install the component. Additionally, many known systems require that a light portal or window be installed through a wall of the combustor casing, the combustion liner, and/or the flow sleeve of the combustor. Accordingly, a portion of such combustor wall(s) must be removed, which can result in significant leakage and wear issues.

Accordingly, a system for controlling combustor operating conditions based on flame detection that can be easily installed within a combustor without removing portions of the combustion casing, combustion liner and/or the flow sleeve would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter discloses a system including a combustor having an end cover and at least one fuel nozzle assembly extending from an inner face of the end cover. A cartridge may extend through the end cover and into the fuel nozzle assembly. The cartridge may define an opening for receiving light emitted from within the combustor. Additionally, a fiber optic cable may be disposed within the cartridge and may be configured to capture at least a portion of the light received through the opening.

In another aspect, the present subject matter discloses a method including inserting a cartridge through an end cover of a combustor and into a fuel nozzle assembly of the combustor and capturing light emitted from the combustor with a fiber optic cable disposed within said cartridge.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a cross-sectional view of one embodiment of a system in accordance with aspects of the present subject matter;

FIG. 2 illustrates a cross-sectional view of one embodiment of a sensor assembly suitable for use with the system shown in FIG. 1, particularly illustrating the sensor assembly installed within a fuel nozzle assembly of a combustor;

FIG. 3 illustrates a partial, cross-sectional view of the embodiment of the sensor assembly shown in FIG. 2;

FIG. 4 illustrates a perspective view of the embodiment of the sensor assembly shown in FIGS. 2 and 3; and FIG. 5 illustrates a partial, cross-sectional view of another embodiment of a sensor assembly suitable for use with the system shown in FIG. 1

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to a system and method for controlling operating conditions of a gas turbine combustor based on the detection of light from the combustor's flames. The disclosed system generally includes a sensor assembly adapted to be installed within a fuel nozzle assembly of a gas turbine combustor such that light (e.g., ultraviolet and/or visible light) emitted from the combustor's flames may be captured and transmitted for subsequent detection, measurement and/or analysis. Thus, in several embodiments, the sensor assembly may include a sensor cartridge configured to be breech-loaded within the fuel nozzle assembly. For example, the sensor cartridge may be configured to be loaded within the fuel nozzle assembly through an end cover of the combustor. Additionally, a lens-coupled fiber optic cable may be disposed within the sensor cartridge and may be configured to transmit the light emitted from the combustor's flame to a light detector. The light detector may be configured to detect and/or measure a characteristic of the light transmitted through the lens-coupled fiber optic cable, such as the intensity and/or the spectral emissions of the light. Further, the light detector may be coupled to a controller configured to analyze the output of the light detector in order to determine one or more operating conditions of the combustor. For example, based on the light intensity and/or spectral emissions, the controller may be configured to determine the flame temperature within the combustor and/or detect the onset of a lean blow-out (LBO) event. Moreover, the controller may be adapted to adjust an operating parameter of the combustor, such as the fuel flow rate to the combustor, in order to correct and/or prevent any undesirable operating conditions.

It should be appreciated that, by breech-loading the sensor cartridge within the fuel nozzle assembly, the entire sensor assembly may be quickly and easily installed and/or removed from the combustor. As such, the time and costs required to install, repair and/or replace the sensor assembly may be significantly reduced. For example, in several embodiments, the sensor assembly may be installed and/or removed without accessing the interior of the combustor, such as by configuring the sensor cartridge to be loaded through the end cover of the combustor. Additionally, by breech-loading the sensor cartridge within the fuel nozzle assembly, the issues associated with mounting the sensor assembly through the combustion casing, the flow sleeve and/or the combustion liner of the combustor (e.g., leakage and wear) may be avoided.

It should also be appreciated by those of ordinary skill in the art that numerous advantages may be provided by a system that properly detects and controls the operating conditions of a gas turbine combustor. For example, by determining the flame temperature within the combustor, over-firing conditions may be prevented, resulting in improved component life. Additionally, accurate information regarding the flame temperature may enable a reduction in the cooling flow margins and, thereby, increase combustor efficiency. Moreover, lower emissions may be achieved through a controlled flame temperature. Similarly, by providing the ability to detect the onset of a LBO event (e.g., by detecting flame dynamics such as flickering of the flame within the combustor), suitable preventative actions may be taken to prevent the LBO event from occurring, thereby enhancing the operation of the combustor.

Referring now to the drawings, FIG. 1 illustrates a partial, cross-sectional view of one embodiment of a gas turbine system 10 in accordance with aspects of the present subject matter. The turbine system 10 generally includes a compressor section 12, a combustion section 14 and a turbine section 16. The compressor section 12 generally includes a compressor, represented by the illustrated compressor vanes or blades 18, configured to pressurize air flowing into the turbine system 10. The pressurized air discharged from the compressor section 12 may flow into the combustion section 14, which is generally characterized by a plurality of combustors 20 (one of which is illustrated) disposed around an annular array about the axis of the engine. The pressurized air may then be mixed with fuel within each combustor 20 and combusted. Hot gases of combustion may then flow from each combustor 20 to the turbine section 16 in order to drive the turbine system 10 and generate power.

Each combustor 20 of the combustion section 14 may generally include a substantially cylindrical combustion casing 22 secured to a portion of a gas turbine casing 24, such as a compressor discharge casing or a combustion wrapper casing. Additionally, an end cover assembly 26 may be secured to an upstream end of the combustion casing 22. The end cover assembly 26 may generally include an end cover 28 and a plurality of fuel nozzle assemblies 30 coupled to the end cover 28. For example, in one embodiment, each combustor 20 may include six fuel nozzle assemblies 30, with five fuel nozzle assemblies 30 being disposed in a circular array about the longitudinal axis of the combustor 20 and a center fuel nozzle assembly 30 arranged coaxially with the longitudinal axis. Alternatively, each combustor 20 may include fewer than six fuel nozzle assemblies 30 or greater than six fuel nozzle assemblies 30, with such assemblies 30 being arranged in any suitable manner within the combustor. Additionally, the end cover assembly 26 may include a plurality of tubes, manifolds, associated valves and the like (not shown) for feeding gaseous fuel, liquid fuel, air and/or water into the fuel nozzle assemblies 30. For example, distribution tubes or pipes (not shown) may be mounted through the end cover 28 in order to supply fuel, air and/or water into the each of the fuel nozzle assemblies 30.

Each combustor 20 may also include an internal flow sleeve 32 and a combustion liner 34 substantially concentrically arranged within the flow sleeve 32. The combustion liner 34 may generally define a substantially cylindrical combustion chamber 36, wherein fuel and air are injected and combusted to produce hot gases of combustion. Additionally, both the flow sleeve 32 and the combustion liner 34 may extend, at their downstream ends, to a double walled transition piece 38, including an impingement sleeve 40 and an inner duct 42 disposed radially inwardly from the impingement sleeve 40. In particular, the combustion liner 34 may be coupled at its downstream end to the inner duct 42 such that the combustion liner 34 and the inner duct 42 generally define a flowpath for the hot gases of combustion flowing from each combustor 20 to the turbine section 16 of the turbine system 10. Moreover, the flow sleeve 32 may be coupled at its downstream end to the impingement sleeve 40 such that the flow sleeve 32 and the impingement sleeve 40 generally define a flowpath for the pressurized air discharged from the compressor section 12 of the turbine system 10. For example, the impingement sleeve 40 may define a plurality of cooling holes (not shown) configured to permit the pressurized air to enter the radial space defined between the inner duct 42 and the impingement sleeve 40.

It should be appreciated that, in alternative embodiments, the combustors 20 of the turbine system 10 need not be configured exactly as described above and illustrated herein. Rather, each combustor 20 may generally have any suitable configuration that permits fuel or an air/fuel mixture to be combusted and transported to the turbine section 16 in order to drive the turbine system 10 and/or generate power.

Referring still to FIG. 1, the turbine system 10 may also include one or more sensor assemblies 44 installed within one or more of fuel nozzle assemblies 30 of each combustor 20. For example, in embodiments in which the combustors 20 include six fuel nozzle assemblies 30, a sensor assembly 44 may be installed within one, some or all six of the fuel nozzle assemblies 30. In general, the sensor assembly 44 may include a sensor cartridge 46, a fiber optic cable 48 and a lens 50 configured to capture and/or transmit light emitted from the combustion chamber 36 of a combustor 20. In particular, the sensor cartridge 46 may be configured to be mounted within one of the fuel nozzle assemblies 30 such that, as combustion occurs within the combustion chamber 36, light emitted from the combustor's flames may be received by and pass through the lens 50 mounted within the cartridge 46. The light received by and passing though the lens 50 may then captured by and transmitted through the fiber optic cable 48 of the sensor assembly 44.

The turbine system 10 may also include a light detector 52 configured to receive the light captured and transmitted by the sensor assembly 44. Specifically, the fiber optic cable 48 of the sensor assembly 44 may be optically coupled to the light detector 52 such that the light transmitted through fiber optic cable 48 may be received by the light detector 52. In general, the disclosed light detector 52 may be configured to detect and/or measure the properties of the light transmitted by the fiber optic cable 48. For example, the light detector 52 may be capable of detecting and/or measuring the intensity and/or the spectral emissions of the transmitted light. Thus, it should be appreciated that the light detector 52 may generally comprise any suitable light detecting apparatus and/or any suitable light measuring apparatus known in the art. For example, in one embodiment, the light detector 52 may comprise a spectrometer adapted to detect and measure one or more properties of visible, ultraviolet and/or infrared light. In another embodiment, the light detector 52 may comprise a photomultiplier tube (PMT) or an assembly of PMTs configured to detect and measure one or more properties of visible, ultraviolet and/or infrared light.

In addition, the light detector 52 may be communicatively coupled to a controller 54. The controller 54 may generally be configured to analyze the output provided by the light detector 52 in order to determine an operating condition of the combustor 20. For example, the controller 54 may be configured to implement equations, transfer functions, algorithms and/or the like which enable the controller 54 to correlate the intensity and/or spectral emissions of the light measured by the light detector 52 to the flame temperature within the interior of the combustor 20. Additionally, the controller 54 may include equations, transfer functions and/or algorithms that, when implemented, configure the controller 54 to identify the precursors of a LBO event. In other embodiments, the controller may be configured to determine various other operating conditions of the combustor based upon the output of the light detector, such as changes in fuel composition, flashback/flame holding, fuel maldistribution and the like.

It should be readily appreciated that the development of such equations, transfer functions and/or algorithms is generally within the capability of those skilled in the art, and therefore will not be discussed in any detail herein. However, as an example, the flame temperature within the interior of the combustor 20 may be determined by developing a suitable transfer function relating temperature to the intensity and/or the spectral emissions of the light detected and measured by the light detector 52. Thus, in one embodiment, a combustor 20 may be operated under controlled settings in which the flame temperature is known. In such an embodiment, the light detector 52 may be configured to detect and measure the light intensity of one or more chemical species (e.g., CH* and/or OH*) resulting from the reactions occurring within the combustor 20. The measured light intensity(ies) may then be correlated to the known flame temperatures in order to develop a suitable transfer function. As another example, the precursors of a LBO event may be detected by developing a suitable algorithm for analyzing the flame dynamics occurring within a combustor 20. For instance, the onset of a LBO event may often be characterized by flickering of the flame within the combustor 20, thereby creating sudden increases and decreases in the intensity and/or spectral emissions of the light emitted from the combustion chamber 36. As such, the light detector 52 may be configured to detect and measure such sudden variations in the light. The controller 54 may then be adapted to compare the magnitude and/or amount of such variations to a predetermined threshold in order to determine the likelihood of a LBO event occurring.

The controller 54 of the disclosed turbine system 10 may also be communicatively coupled to one or more of the various components of the turbine system 10 in order to permit a preventative and/or corrective action to be performed. Specifically, the controller 54 may be configured to adjust an operating parameter of the turbine system 10 based upon the determined operating condition in order to prevent and/or correct any undesirable operating conditions. For example, the controller 54 may be configured to adjust the fuel flow rate into the combustor 20 and/or adjust the fuel split or fuel distribution into the fuel nozzle assemblies 30 in order to reduce excessive flame temperatures and/or prevent a LBO event. In other embodiments, the controller 54 may be configured to adjust other combustion settings, adjust the inlet guide vane angle, adjust inlet bleed heat, active a water injection system of the turbine system 10 and/or take any other suitable preventative and/or corrective actions known in the art.

It should be appreciated that the controller 54 may generally comprise any suitable processing equipment known in the art that permits the turbine system 10 to be controlled and/or operated as described herein. For example, the controller 54 may comprise any suitable computer, computer system and/or turbine control system having a processor(s) configured to implement programs (e.g., computer readable instructions stored in the controller's memory) that, when executed, control the operation of the turbine system 10. Additionally, as indicated above, the controller 54 may be configured to determine an operating condition of the combustor 20 based upon the properties of the light transmitted through the fiber optic cable 48 and detected and/or measured by the light detector 52. Thus, the controller 54 may also include stored programs having suitable equations, transfer functions and/or algorithms that, when implemented by the controller's processor(s), enable the controller 54 to determine such operating conditions.

Further, as indicated above, the turbine system 10 may generally include any number of sensor assemblies 44, such as by having a sensor assembly 44 installed within each fuel nozzle assembly 30. As such, it should be appreciated that the light detector 52 may be configured to detect and/or measure one or more of the properties of the light transmitted through the fiber optic cable 48 of each sensor assembly 44. The controller 54 may, in turn, be configured to analyze the output from the light detector 44 in order to determine one or more operating conditions of the combustor 20 based upon analysis of the outputs for each sensor assembly 44 individually or based upon analysis of the outputs in combination. For example, the controller 54 may be configured to average the flame temperature detected by each sensor assembly 44 in order to approximate the actual flame temperature within the combustor 20. Moreover, the controller 54 may be capable of analyzing and/or comparing the variability in the output provided by the light detector 52 for each sensor assembly 44. Specifically, the controller 54 may be equipped to detect fuel nozzle-to-fuel nozzle or can-to-can variations in the flame temperature and/or the flame dynamics. As such, the controller 54 may be utilized to make fuel nozzle specific adjustments, such as by adjusting the fuel split to a particular fuel nozzle assembly 30 or set of fuel nozzle assemblies 34, in order to correct such variations.

Referring now to FIGS. 2-4, there is illustrated one embodiment of a sensor assembly 44 suitable for use with the disclosed turbine system 10. In particular, FIG. 2 illustrates a cross-sectional view of the sensor assembly 44 installed within a fuel nozzle assembly 30 of a combustor 20 of the turbine system 10. FIG. 3 illustrates a partial, cross-sectional view of the sensor assembly 44 shown in FIG. 2. FIG. 4 illustrates a perspective view of the sensor assembly 44 shown in FIGS. 2 and 3.

In general, the sensor assembly 44 of the present subject matter may be configured to be mounted or otherwise installed within any suitable fuel nozzle assembly 30 known in the art. Thus, it should be appreciated that the particular fuel nozzle configuration shown FIG. 2 is provided for illustrative purposes only to place the disclosed sensor assembly 44 in one exemplary location within the turbine system 10. Accordingly, one of ordinary skill in the art should understand that the disclosed turbine system 10 need not be limited to any particular type of fuel nozzle configuration.

As shown in FIG. 2, the fuel nozzle assembly 30 generally includes a nozzle body 56 having a first end 57 attached to an inner face 71 of the end cover 28 of the combustor 20 and a second end 58 defining a nozzle tip 59. The first end 57 of the nozzle body 56 may generally be configured to be attached to the inner face 71 of the end cover 28 using any suitable means. For example, in one embodiment, a flange 60 may be defined at the first end 57 in order to permit the nozzle body 56 to be attached to the inner face 71, such as by bolting or welding the flange 60 to the inner face 71. Alternatively, the flange 60 and/or the nozzle body 56 may be formed integrally with the end cover 28. The fuel nozzle assembly 30 may also include an inlet 61 configured to receive the pressurized air flowing from the compressor section 12 (FIG. 1) of the turbine system 10. In one embodiment, the inlet 61 may comprise an inlet flow conditioner configured to improve the air flow velocity distribution through the nozzle assembly 30. The pressurized air flowing through the inlet 61 may generally be directed to a plurality of air swirler vanes 62 configured to impart a swirling pattern to the air so as to facilitate mixture of the air with fuel. Additionally, each swirler vane 62 may define a plurality of fuel injection ports or holes 63 configured to inject fuel into the air stream. The air and fuel may then flow into a premixing zone or premixing annulus 64, defined by an outer burner tube 65 and an outer tube 66 of the nozzle body 56, wherein the air and fuel are mixed prior to entering the combustion chamber 36.

As is generally understood, the nozzle body 56 of the fuel nozzle assembly 30 may include a plurality of concentrically arranged passages 67, 68, 69 for flowing flow a fluid, such as air, fuel and/or water, in the direction of the nozzle tip 59 for injection into the combustion chamber 36 of the combustor 20. For example, in the illustrated embodiment, a first inner tube 70 may be arranged concentrically within the outer tube 66 of the nozzle body 56, creating a first annular passage 67 for supplying a fluid (e.g., curtain air) to the nozzle tip 59. For example, a small portion of the pressurized compressor air flowing towards the inlet 61 may enter the first annular passage 67 through a plurality of circumferentially arranged channels or holes 72 extending between the first annular passage 67 and an outer surface 73 of the outer burner tube 65. Additionally, a second inner tube 74 may generally be arranged concentrically within the first inner tube 70. As such, a second annular passage 68 may generally be defined between the first and second inner tubes 70, 74. The second annular passage 68 may also be configured to supply a fluid (e.g., diffusion air or fuel) through the nozzle body 56. As such, the second annular passage 68 may be in flow communication with a fluid source (not shown), such as an air or fuel source coupled to the second annular passage 68 through a distribution tube (not shown) mounted through the end cover 28, to permit the fluid to be supplied to the passage 68. Additionally, the second inner tube 74 may, itself, define a third annular passage 69 (hereinafter referred to as the "central passage 69" of the nozzle body 56) disposed coaxially with the central axis 75 of the fuel nozzle assembly 30. Further, the nozzle body 56 may define one or more premix fuel passages 76 extending between the end cover 28 and the air swirler vanes 62. The premix fuel passages 76 may generally be in flow communication with a premix fuel source (not shown) so as to permit fuel to flow into the nozzle body 56 and be expelled through the fuel injection ports 63 defined in the air swirler vanes 62.

It should be readily appreciated that, in alternative embodiments, the nozzle body 56 of the premix fuel nozzle assembly 30 may generally have any other suitable configuration known in the art and, thus, need not have the exact configuration described above and illustrated herein. For example, the nozzle body 56 may generally include any number of tubes 66, 70, 74 and passages 67, 68, 69 having any suitable configuration that permits one or more fluids to be supplied through the nozzle body 56.

Referring still to FIG. 2, as indicated above, the sensor assembly 44 of the present subject matter may generally include a sensor cartridge 46, a fiber optic cable 48, and a lens 50. In general, the sensor cartridge 46 may be configured to be installed within the central passage 69 of the nozzle body 56. Thus, in the illustrated embodiment, the sensor cartridge 46 may generally be configured extend longitudinally along the central axis 75 of the nozzle body 56. For example, as shown, the sensor cartridge 46 may include a base end 77 disposed generally adjacent to the end cover 28 of the combustor 20 and a tip end 78 disposed generally adjacent to the nozzle tip 59. As such, the light emitted from the combustor's flames within the combustion chamber 36 may be received at the tip end 78 of the sensor cartridge 46 and transmitted out the base end of the cartridge 46 through the fiber optic cable 48.

In general, the sensor cartridge 46 may have any suitable configuration that allows the cartridge 46 to be loaded or otherwise installed within the central passage 69. However, in several embodiments, the sensor cartridge 46 may be configured to he breech-loaded within the central passage 69. By the term "breech-loaded," it is meant that the cartridge 46 may be installed within the central passage 69 through the back end 57 of the nozzle body 56 and/or through the end cover 28. Thus, in the illustrated embodiment, the sensor cartridge 46 may be configured to be loaded within the central passage 69 through a corresponding passage 79 defined in the end cover 28. For example, the passage 79 may be defined in the end cover 28 so as to be aligned with the central passage 69 and, thus, disposed coaxially with the central axis 75 of the fuel nozzle assembly 30. As such, sensor cartridge 46 may be inserted through the passage 79 and into the fuel nozzle assembly 30. It should be appreciated that the passage 79 may correspond to a pre-existing passage defined in the end cover 28, such as a pre-existing passage configured to supply a fluid through the central passage 69. Alternatively, the passage 79 may be formed in the end cover 28 to accommodate breech-loading of the sensor cartridge 46.

Additionally, it should be appreciated that the sensor cartridge 46 may generally define any suitable shape and/or have any suitable dimensions that permit the cartridge 46 to be inserted through the passage 79. For instance, in one embodiment, the sensor cartridge 46 may be configured to define a shape and may have dimensions that generally correspond to the shape and dimensions of the passage 79. Thus, in the illustrated embodiment, the sensor cartridge 46 may define a substantially cylindrical shape generally corresponding to the circular shape of the passage 79 and may have a diameter or height 80 generally corresponding to the diameter or height of the passage 79. As such, the sensor cartridge 46 may generally occupy the entire cross-sectional area of the passage 79 when the cartridge 46 is installed within the central passage 69. Alternatively, the sensor cartridge 46 and passage 79 may have differing shapes and/or dimensions. For example, in one embodiment, the diameter or height 80 of the sensor cartridge 46 may be less than the diameter or height of the passage 79 so that a radial passage or gap is defined between the sensor cartridge 46 and the end cover 28.

Additionally, in several embodiments, the sensor cartridge 46 may be configured to be attached or otherwise secured to the end cover 28 of the combustor 20. For example, in one embodiment, the base end 77 of the sensor cartridge 46 may define an outwardly extending flange 81 configured to be attached to the end cover 28. Thus, as shown, the sensor cartridge 46 may be configured such that, when the cartridge 46 is loaded into the central passage 69, the flange 81 is engaged against an outer face 82 of the end cover 28. The flange 81 may then be secured to the outer face 82 using any suitable means, such as by bolting the flange 81 to the outer face 82 through a plurality of bolt holes 99 (FIG. 4) defined in the flange 81 or by welding the flange 81 to the outer face 82. In alternative embodiments, it should be appreciated that the sensor cartridge 46 may generally have any other suitable configuration that permits the cartridge 46 to be attached to the end cover 28. For instance, in one embodiment, the cartridge 46 may be configured to be press-fit into the passage 79 defined in the end cover 28.

As indicated above, numerous advantages may be provided to the disclosed system 10 by breech-loading the sensor cartridge 46 within the fuel nozzle assembly 30. For example, the time and costs required to install, repair and/or replace the sensor assembly 44 may be reduced significantly. Specifically, in the illustrated embodiment, the sensor assembly 44 may be installed within the nozzle body 56 by simply inserting the sensor cartridge 46 into the central passage 69 through the corresponding passage 79 defined in the end cover 28 and attaching the flange 81 to the outer face 82 of the end cover 28. Similarly, the sensor assembly 44 may be removed by simply detaching the flange 81 from the end cover 28 and pulling the assembly 44 out through the passage 79.

Referring still to FIGS. 2-4, the sensor cartridge 46 may also be configured to serve as the outer housing or casing of the sensor assembly 44 and, thus, may define an inner passage or channel for receiving the fiber optic cable 48 and the lens 50. For example, in the illustrated embodiment, the sensor cartridge 46 may configured as a tubular member and may include an outer wall 83 defining an inner channel 84. The inner channel 84 may generally be configured to extend longitudinally within the sensor cartridge 46. Thus, as shown, in one embodiment, the inner channel 84 may be configured to extend along the entire length of the sensor cartridge 46, such as by extending between the base and tip ends 77, 78 of the cartridge 46. As such, the portion of the inner channel disposed at the tip end 78 may generally define a tip opening 85 for receiving the light emitted from the combustor's flames. Accordingly, the lens 50 may generally be mounted at location generally adjacent to the tip opening 85 such that the light received within the opening 85 passes through the lens 50. Additionally, the portion of the inner channel 84 disposed at the base end 77 of the cartridge 46 may generally define a base opening 86 through which the fiber optic cable 48 may be disposed. For example, as indicated above, the fiber optic cable 48 may generally be configured to be optically coupled to the light detector 52 (FIG. 1) of the turbine system 10. Thus, in the illustrated embodiment, the fiber optic cable 48 may extend from a location within the inner channel 84 through the base opening 86 to a location exterior of the cartridge 46 at which the light detector 52 is disposed. It should be appreciated that, in such an embodiment, the portion of the inner channel 84 defined at or adjacent the base opening 86 may be sealed around the fiber optic cable 48, such as by using any suitable seal or sealing mechanism, to prevent the leakage of fluid through the base opening 86.

Moreover, in several embodiments of the present subject matter, the sensor cartridge 46 may be configured to receive a fluid, such as air, hydrogen, nitrogen, liquid fuel, gaseous fuel, water, steam and/or any other suitable liquid and/or gas, for cooling the cartridge 46, the fiber optic cable 48, the lens 50 and/or one or more components of the fuel nozzle assembly 30. Specifically, the sensor cartridge 46 may be configured such that the inner channel 84 is in flow communication with a fluid source. For example, the inner channel 84 may be in flow communication with one or more of the annular passages 67, 68 defined in the nozzle body 56 such that the fluid flowing through such annular passage(s) 67, 68 may be directed into the inner channel 84. Thus, as shown in the illustrated embodiment, a plurality of cross-over passageways 87 may be defined around the circumference of both the second annular passage 68 and the sensor cartridge 46 to permit the fluid supplied through the annular passage 68 to enter the inner channel 84. In other embodiments, the sensor cartridge 46 may have any other suitable configuration that allows the fluid flowing through one or more of the annular passages 67, 68 to be directed into the inner channel 84. Additionally, in alternative embodiments, the sensor cartridge 46 may be configured to receive a fluid from any other suitable fluid source. For instance, as will be described below with reference to FIG. 5, the sensor cartridge 46 may define a fluid inlet 103 (FIG. 5) in an area adjacent to the base end 177 of the cartridge 46 to permit a fluid to be supplied through the cartridge 46.

In addition to providing cooling to the components of the sensor assembly 44 and/or the fuel nozzle assembly 30, the fluid supplied through the sensor cartridge 46 may also serve to enhance the combustion process occurring within the combustor 20, such as by increasing the combustion efficiency and/or lowering emissions. Thus, in several embodiments, the sensor cartridge 46 may be configured to inject the fluid flowing through the inner channel 84 into the combustion chamber 36. For example, as particularly shown in FIG. 3, one or more fluid outlets 88 may be defined between the inner channel 84 and an outer surface 89 of the sensor cartridge 46 for expelling the fluid supplied through inner channel 84 out the tip end 78 of the cartridge 46 and into the combustion chamber 36. As such, the fluid may serve as atomizing air, diffusion air, diffusion fuel and/or the like.

It should be appreciated that the fluid outlets 88 defined in the sensor cartridge 46 may generally have any suitable configuration that permits the fluid flowing through the inner channel 84 to be expelled from the cartridge 46. For example, in the illustrated embodiment, the fluid outlets 88 may be configured so as to extend from the inner channel 84 to an angled surface 89 defined adjacent to the tip end 78. In other embodiments, the sensor cartridge 46 need not define such an angled surface 89 and, thus, the fluid outlets 88 may be configured to extend between the inner channel 84 and any suitable outer surface 89 of the sensor cartridge 46. Additionally, the fluid outlets 88 may be defined within the sensor cartridge 46 so as to have any suitable orientation and/or arrangement. For instance, as shown in FIGS. 3 and 4, the fluid outlets 88 may comprise straight or angled passages disposed annularly about the tip opening 85. Alternatively, the fluid outlets 88 may comprise curved or helical passages configured to wrap around at least a portion of the outer wall 83 of the sensor cartridge 46. Moreover, one or more swirler features (not illustrated) may be defined adjacent to the fluid outlets 88 to impart a swirling pattern to the fluid as it is expelled from the fluid outlets 88.

Referring still to FIGS. 2-4, the lens 50 of the sensor assembly 44 may generally comprise any suitable window or optical element configured to permit light to pass therethrough. Thus, in one embodiment, the lens 50 may simply comprise a light window configured such that the light emitted from the combustion chamber 36 may pass through the lens 50 and into the inner channel 84. In other embodiments, the lens 50 may comprise an optical lens configured to capture the light emitted from the combustion chamber 36 and focus it onto an end face 90 of the fiber optic cable 48. For instance, the lens 50 may comprise a concave lens having a focal length equal to the spacing between the lens 50 and the end face 90 of the fiber optic cable 48. As such, the light captured by the lens 50 may be focused directly onto the fiber optic cable 48. However, in an alternative embodiment, the lens 50 may be configured as a convex lens or any other suitable optical element, such as a prism.

Additionally, the lens 50 may generally be configured to be mounted within inner channel 84 such that the lens is capable of passing and/or capturing at least a portion of the light emitted in the direction of the sensor cartridge 46. For example, in one embodiment, the lens 50 may be mounted directly at the tip end 78 of the sensor cartridge 46 such that the lens 50 is positioned substantially flush within the tip opening 85. Alternatively, as shown in the illustrated embodiment, the lens 50 may be positioned within inner channel 84 so as to be offset from the tip opening 85. Moreover, it should be appreciated that the lens 50 may be mounted within the inner channel 84 using any suitable means. For example, in the illustrated embodiment, the inner channel 83 may have a stepped profile defining an annular flange or ridge 91 against which the lens 50 may be positioned and attached. In such an embodiment, the lens 50 may be mounted against the annular ridge 91 using any suitable attachment mechanisms, such as screws, pins, retaining rings, retaining clips and/or any other suitable retaining features. In other embodiments, it should be appreciated that the inner channel 84 need not define the illustrated stepped profile. For instance, in one embodiment, a groove (not shown) may be defined around the perimeter of the inner channel 84 into which the lens 50 may be securely mounted. In further embodiments, the sensor cartridge 46 and/or lens 50 may have any other suitable configuration that permits the lens 50 to be attached within the inner channel 84.

Further, the disclosed lens 50 may generally be formed from any suitable material. For example, the lens 50 may be formed from a material capable of withstanding the high temperatures occurring within the combustor 20. As such, the lens 50 may generally serve as a heat shield for the fiber optic cable 48 disposed within the inner channel 84. For instance, in several embodiments, the lens 50 may be formed from a material such as sapphire or any other suitable high temperature material. Further, in one embodiment, the outer surface 92 of the lens 50 may include a protective, transparent coating configured to provide increased thermal resistance to the lens 50.

Moreover, the lens 50 may generally have any suitable shape and/or dimensions. However, in one embodiment, the shape and/or dimensions of the lens 50 may generally correspond to the shape and/or dimension of the portion of the inner channel 84 in which the lens 50 is mounted. As such, the lens 50 may be sealed within the inner channel 84, such as by using any suitable seal and/or sealing mechanism, in order to prevent the fluid supplied through the inner channel 84 from flowing past the lens 50. Alternatively, the lens 50 may be configured such that at least a portion of the fluid supplied through the inner channel 83 flows past the lens 50 and is expelled through the tip opening 85.

Additionally, in several embodiments of the present subject matter, the sensor cartridge 46 may include a lens cooling feature for cooling the outer surface 92 of the lens 50. For example, the sensor cartridge 46 may define one or more lens cooling passages 93 for directing at least a portion of the fluid supplied through the inner channel 84 against and/or adjacent to the outer surface 93 of the lens 50. Thus, as particularly shown in FIGS. 3 and 4, a plurality of annularly disposed fluid cooling passages 93 may be defined between the fluid outlets 88 and the inner channel 84 such that a portion of the fluid flowing through the fluid outlets 88 may be directed against and/or adjacent to the outer surface 89 of the lens 50. As such, the fluid may serve as a cooling medium for the outer surface 89 and may also serve to clean any debris and/or contaminants off the outer surface 89. It should be appreciated that, in alternative embodiments, the lens cooling passages 93 may be in direct flow communication with fluid flowing through the inner channel 84 and, thus, need not be defined within the sensor cartridge 46 so as to be connected to the fluid outlets 88.

Referring still to FIGS. 2-4, as indicated above, the fiber optic cable 48 of the sensor assembly 44 may generally be configured to capture and/or transmit the light emitted from the combustor's flames and passing through the lens 50 to the light detector 52 (FIG. 1) of the turbine system 10 in order to permit the properties of such light to be detected and/or measured. Thus, a portion of the fiber optic cable 48 may be disposed exterior of the sensor cartridge 46 such that a first end 94 (FIG. 1) of the fiber optic cable 48 may be optically coupled to the light detector 52. The remainder of the fiber optic cable 48 may disposed within sensor cartridge 46 such that a second end 95 of the fiber optic cable 48 is positioned at a location at which at least a portion of the light passing through the lens 50 may be directed into and captured by an end face 90 of the fiber optic cable 48. For example, in several embodiments, the end face 90 of the fiber optic cable 48 may be disposed directly against an inner surface 96 of the lens 50. In other embodiments, the end face 90 of the fiber optic cable 48 may be spaced apart from the lens 50. For instance, as described above, the fiber optic cable 49 may be spaced apart from the lens 50 a distance generally equal to the focal length of the lens 50.

As used herein, the term "fiber optic cable" may include a fiber optic cable 48 having a single optical fiber or a fiber optic cable 48 configured as a fiber optic bundle and having a plurality of optical fibers. Thus, it should be appreciated that the disclosed fiber optic cable 48 may generally include any number of optical fibers. In general, the optical fiber(s) of the fiber optic cable 48 may be configured the same to similar to any suitable optical fibers known in the art. Thus, the optical fiber(s) may be configured to have any suitable field of view relative to the longitudinal axis of the fiber(s). Additionally, the optical fibers may be formed from any suitable material, such as silica glasses, fluoride glasses, sapphire and the like. Moreover, in several embodiments, the optical fibers may include an outer coating configured to provide thermal protection to the fibers. For example, the optical fibers may be coated with gold, other precious metals and/or any other suitable material that allows the optical fibers to withstand the high temperatures within the fuel nozzle assembly 30.

It should also be appreciated that the fiber optic cable 48 may generally define any suitable dimensions. For example, in the illustrated embodiment, the fiber optic cable 48 may define a diameter or height 97 that permits the fiber optic cable 48 to be disposed and/or mounted within a narrowed portion 98 of the inner channel 84 formed by the stepped profile defined generally adjacent to the tip end 78 of the sensor cartridge 46. However, as indicated above, the sensor cartridge 46 need not define such a stepped profile. Thus, in other embodiments, the fiber optic cable 48 may generally define any suitable diameter or height 97 that permits the fiber optic cable 48 to be inserted within the inner channel 84.

Referring now to FIG. 5, there is illustrates a partial, cross-sectional view of another embodiment of a sensor assembly 144 suitable for use with the disclosed turbine system 10 in accordance with aspects of the present subject matter. In general, the sensor assembly 144 may include many or all of the same or similar components and/or features described above with reference to FIGS. 2-4. Thus, sensor assembly 144 may include a sensor cartridge 146, a fiber optic cable 148 and a lens 150. The sensor cartridge 146 may generally be configured to be breech loaded into and secured within the central passage 69 (FIG. 2) of a fuel nozzle assembly 30. Thus, in one embodiment, the sensor cartridge 146 may define a flange 181 at its base end 177 for attaching the cartridge 146 to the outer face 82 (FIG. 2) of the end cover 28 of the combustor 20. Additionally, the lens 150 of the sensor assembly 144 may be mounted within an inner channel 184 of the sensor cartridge 146 at a location generally adjacent to the tip end 178 of the cartridge 146 such that light emitted from the combustor's flame may pass through the lens 150 and into the inner channel 184. Moreover, the fiber optic cable 148 may be partially disposed within the sensor cartridge 146 such that light passing through the lens 150 may be captured and transmitted by the fiber optic cable 148 to the light detector 52 (FIG. 2).

However, unlike the embodiment described above, the sensor cartridge 146 may define one or more outer channels 101 configured to flow a fluid, such as air, hydrogen, nitrogen, liquid fuel, gaseous fuel, water, steam and/or any other suitable liquid and/or gas, through the senor cartridge 146. In particular, the cartridge 146 may include concentrically arranged walls 183, 102 defining the outer channel(s) 101 and the inner channel 184. For example, in the illustrated embodiment, the sensor cartridge 146 may include an outer wall 183 defining an outer tube of the cartridge 146 and an inner wall 102 defining an inner tube of the cartridge 146. As such, an outer channel 101 may be defined between the outer and inner walls 183, 102 which is disposed radially outwardly from the inner channel 184. In other embodiments, the sensor cartridge may include any number of inner walls 102 defining any number of additional channels 101 disposed radially outwardly from the inner channel 184.

It should be appreciated that the outer channel 101 may generally be in flow communication with a suitable fluid source (not shown) to permit a fluid to be received within the outer channel 101. For example, in one embodiment, a fluid inlet 103 may be defined generally adjacent to the base end 177 of the sensor cartridge 146 (such as by being defined within the flange 181) and may be configured to be coupled to a fluid source. As such, fluid flowing from the fluid source may enter the fluid inlet 103 and may be directed into the outer channel 101. In another embodiment, one or more cross-over passageways (not shown), similar to the passageways 87 described above with reference to FIGS. 2-4, may be defined between the outer channel 101 and one or more annular passages 67, 68 (FIG. 2) of the nozzle body 56 to allow the fluid flowing through the annular passage(s) 67, 68 to be directed into the outer channel 101. In further embodiments, the sensor cartridge 146 may have any other suitable configuration that permits a fluid to be received within the outer channel 101. It should also be appreciated that, in several embodiments, a portion of the fluid received by the sensor cartridge 146 may be directed into the inner channel 184 to provide cooling for the fiber optic cable 148 and the lens 150 of the sensor assembly 144. For instance, the inner channel 184 may be in flow communication with the fluid inlet 103 such that a portion of the fluid flowing through the inlet 103 is directed into the inner channel 184. Alternatively, the inner channel 184 may be coupled to a separate fluid inlet 106 (shown in hidden lines) defined generally adjacent to the base end 177 of the sensor cartridge 146. In further embodiments, the inner channel 184 may be flow communication with the outer channel 101, such as by defining one or more openings (not illustrated) through the inner wall 102.

Additionally, one or more fluid outlets 104 may be defined at a downstream end 105 of the outer channel 101 for injecting the fluid flowing through the outer channel 101 into the combustion chamber 36 of the combustor 20. As such, the fluid may serve to enhance the combustion process occurring within the combustor 20, such as by increasing the combustion efficiency and/or lowering emissions. For example, the fluid may be injected into the combustion chamber 36 as atomizing air, diffusion air, diffusion fuel and/or the like. It should be appreciated that the fluid outlet(s) 104 defined at the downstream end 105 of the outer channel 101 may generally have any suitable configuration. For example, in one embodiment, the downstream end 105 of the outer channel 101 may extend fully to the outer surface 189 of the sensor cartridge 146 such that the downstream end 106 defines a fluid outlet 104 around the tip opening 185 at or adjacent to the tip end 178. Alternatively, as shown in FIG. 5, the downstream end 105 of the outer channel 101 may terminate within the sensor cartridge 146 such that one or more fluid outlets 104 may be defined between the outer channel 101 and the outer surface 189 of the sensor cartridge 146. For instance, a plurality of straight or angled fluid outlets 104 may extend between the outer channel 101 and the outer surface 189 so as to be disposed annularly about the tip opening 185.

Additionally, similar to the embodiment described above, one or more lens cooling passages 107 may be defined in the sensor cartridge 146 to permit the outer surface 192 of the lens 150 to be cooled and/or cleaned. For example, the lens cooling passages 107 may be in flow communication with the fluid outlets 104 and/or the outer channel 101 such that a portion of the fluid flowing through the fluid outlets 104 and/or the outer channel 101 may be directed into the lens cooling passages.

It should be appreciated that, in embodiments in which fluid is also directed through the inner channel 184, a plurality of fluid outlets (not shown) may also be defined between the inner channel 184 and the outer surface 189 of the sensor cartridge 146. Alternatively, the inner channel 184 may be flow communication with the outer channel 101 and/or the fluid outlets 104 to permit the fluid to be expelled from the inner channel. In further embodiments, the fluid flowing through the inner channel 184 may be expelled through and/or around a portion of the lens 150.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system, comprising:
a combustor including an end cover and at least one fuel nozzle assembly extending from a first end disposed at an inner face of said end cover to a second end defining a nozzle tip, said end cover extending radially and circumferentially around an opening defined within an outer casing surrounding said combustor, said at least one fuel nozzle assembly extending along a central axis from said first end to said second end, said at least one fuel nozzle assembly defining a central passage extending along said central axis, said at least one fuel nozzle includes a plurality of concentrically arranged passages surrounding said central passage;
a cartridge extending through said end cover and into said central passage of said at least one fuel nozzle assembly such that said cartridge extends longitudinally within said central passage along said central axis, said cartridge defining an opening for receiving light emitted from within said combustor assembly, wherein said cartridge is breech loaded into said central passage of said at least one fuel nozzle assembly through an opening in said end cover and is removable from said central passage of said at least one fuel nozzle assembly; and
a fiber optic cable disposed within said cartridge, said fiber optic cable being configured to capture at least a portion of the light received through said opening.

2. The system of claim 1, wherein a portion of said cartridge is configured to engage an outer face of said end cover.

3. The system of claim 2, wherein said cartridge defines a flange, said flange being attached to said outer face.

4. The system of claim 1, wherein said cartridge extends within said central passage so as to be coaxially aligned with said central axis.

5. The system of claim 1, further comprising a lens mounted within said cartridge, said lens configured to focus at least a portion of the light received through said opening onto an end face of said fiber optic cable.

6. The system of claim 1, further comprising a light detector coupled to said fiber optic cable, said light detector being configured to measure a characteristic of the light transmitted through said fiber optic cable.

7. The system of claim 6, further comprising a controller communicatively coupled to said light detector, said controller being configured to analyze an output of said light detector to determine an operating condition of said combustor.

8. The system of claim 7, wherein said operating condition comprises at least one of a flame temperature and a lean blow-out precursor.

9. The system of claim 7, wherein said controller is further configured to adjust an operating parameter of said combustor based on said operating condition.

10. The system of claim 1, wherein a fluid is supplied through at least a portion of said cartridge, said fluid being directed through at least one of an inner channel and an outer channel of said cartridge.

11. The system of claim 10, further comprising a plurality of fluid outlets defined in said cartridge, said fluid being expelled from said cartridge through said plurality of fluid outlets.

12. A method, comprising:
inserting a cartridge through an end cover of a combustor and into a central passage defined within a fuel nozzle assembly of said combustor, said cartridge including a cylindrical tube sized to insert and remove from said central passage through an opening in said end cover, said fuel nozzle assembly extending from a first end disposed at an inner face of said end cover to a second end defining a nozzle tip, said fuel nozzle assembly extending along a central axis from said first end to said second end, said fuel nozzle includes a plurality of concentrically arranged passages surrounding said central passage, said central passage being defined within said fuel nozzle assembly along said central axis such that, when the cartridge is inserted into said central passage, said cartridge extends longitudinally along said central axis; and
capturing light emitted from said combustor with a fiber optic cable disposed within said cartridge.

13. The method of claim 12, further comprising attaching said cartridge to said end cover.

14. The method of claim 12, further comprising measuring a characteristic of the light captured by said fiber optic cable.

15. The method of claim 14, further comprising analyzing the characteristic in order to determine an operating condition of said combustor.

16. The method of claim 15, wherein said operating condition comprises at least one of a flame temperature and a lean blowout precursor.

17. The method of claim 15, further comprising controlling an operating parameter affecting combustion within said combustor based on said operating condition.

18. The method of claim 17, wherein said operating parameter comprises at least one of fuel flow rate to said combustor and a fuel split to said fuel nozzle assembly.

19. The system of claim 11, further comprising at least one lens cooling passage in flow communication with at least one of the plurality of fluid outlets such that at least a portion of the fluid is directed through the at least one lens cooling passage in a direction of a lens mounted within said cartridge.

20. The method of claim 12, further comprising directing a fluid through said cartridge to cool at least one of said cartridge, said fiber optic cable or a lens mounted within said cartridge.

* * * * *